United States Patent
Nakao et al.

[11] Patent Number: 5,855,558
[45] Date of Patent: Jan. 5, 1999

[54] ULTRASONIC PROBE AND ULTRASONIC DIAGNOSTIC APPARATUS

[75] Inventors: Narutaka Nakao; Kenichi Hayakawa; Nobuyuki Hayashi, all of Kawasaki, Japan

[73] Assignee: Fujitsu Limited, Kawasaki, Japan

[21] Appl. No.: 837,330

[22] Filed: Apr. 11, 1997

[30] Foreign Application Priority Data

Sep. 26, 1996  [JP]  Japan .................................. 8-254629

[51] Int. Cl.$^6$ ....................................................... A61B 8/00
[52] U.S. Cl. .......................................................... 600/459
[58] Field of Search ........................ 128/662.05, 660.01; 600/444, 443; 680/459

[56] References Cited

U.S. PATENT DOCUMENTS

| | | | |
|---|---|---|---|
| 4,167,180 | 9/1979 | Kossoff | 600/449 |
| 4,669,482 | 6/1987 | Ophir | 600/445 |
| 4,899,756 | 2/1990 | Sonek | 128/662.05 |
| 4,949,310 | 8/1990 | Smith et al. | 128/660.01 |
| 5,052,396 | 10/1991 | Wedel et al. | 128/662.05 |
| 5,076,279 | 12/1991 | Arenson et al. | 128/662.05 |
| 5,090,414 | 2/1992 | Takano | 128/662.05 |
| 5,427,108 | 6/1995 | Bollinger | 128/662.05 |
| 5,672,172 | 9/1997 | Zupkas | 128/662.05 |

FOREIGN PATENT DOCUMENTS

5-33708   5/1993  Japan .
5-317309  12/1993  Japan .

*Primary Examiner*—Marvin M. Lateef
*Assistant Examiner*—Maulin Patel
*Attorney, Agent, or Firm*—Staas & Halsey

[57] ABSTRACT

An ultrasonic probe having a first ultrasonic transmitter-receiver head having a plurality of first ultrasonic transducers carrying transmission and reception of ultrasounds, the plurality of first ultrasonic transducers being arranged in a predetermined first direction. The ultrasonic probe also has a second ultrasonic transmitter-receiver head, detachably loaded onto the first ultrasonic transmitter-receiver head, having a plurality of second ultrasonic transducers carrying transmission and reception of ultrasounds, the plurality of second ultrasonic transducers being arranged in a second direction intersecting the first direction when loaded. The second ultrasonic transmitter-receiver head monitors a state that a puncture needle to be punctured inside a subject is inserted into the inside of the subject. According to the present invention it is possible to implement an ultrasonic probe suitable for both use of a normal diagnosis and a puncture and is capable of contributing to a reduction of the cost. An ultrasonic diagnostic apparatus having such an ultrasonic probe is also described.

8 Claims, 10 Drawing Sheets

ULTRASONIC PROBE AND ULTRASONIC DIAGNOSTIC APPARATUS

BACKGROUND OF THE INVENTION

1. Field of the Invention

The present invention relates to an ultrasonic probe which is adapted to be put to a subject, and which transmits ultrasounds to the inside of the subject and which receives ultrasounds reflected inside of the subject. The present invention also relates to an ultrasonic diagnostic apparatus in which the ultrasonic probe is used to transmit and receive ultrasounds and images within the subject are produced and displayed in accordance with received signals derived through receiving ultrasounds with the ultrasonic probe.

2. Description of the Related Art

Hitherto, there has been used for diagnoses of diseases within the subject an ultrasonic diagnostic system in which ultrasonic beams are transmitted inside of the subject, particularly, the human body, and ultrasounds reflected at the inside of tissues in the human body and the boundary between tissue-to-tissue are received in the form of received signals, so that images in the human body involved in the received signals are formed.

Such an ultrasonic diagnostic system comprises, usually, a main frame of the ultrasonic diagnostic system and an ultrasonic probe connected through a cable to the main frame. On the tip of the ultrasonic probe, there are arranged a lot of ultrasonic transducers (e.g. 128 pieces) in which when drive signals are input, ultrasounds are transmitted in accordance with the drive signals, and the ultrasounds reflected inside the subject are picked up to generate received signals. To derive ultrasonic images within the subject, the tip of the ultrasonic probe is put to a surface of the subject. Drive signals generated in the main frame of the ultrasonic diagnostic system are fed to the ultrasonic transducers so that ultrasound is transmitted in a direction along one scan line extending within the subject and the ultrasound reflected inside the subject is picked up to generate a received signal carrying information as to the inside of the subject along the one scan line. This performance is repeated (scanned) while the scan line is shifted in a direction along which the ultrasonic transducers are arranged. In this manner, there is formed an ultrasonic image (tomographic image) within a section of the inside of the subject as to the direction along which the ultrasonic transducers are arranged. The tomographic image thus formed is displayed on an image display apparatus of the main frame of the ultrasonic diagnostic system, or may be recorded on a video tape and the like.

An ultrasonic diagnostic system is usually provided with a function of obtaining tomographic images within the subject, and in addition has a function of obtaining images representative of a blood flow distribution. However, these functions are well known in technology. Hence, there will be omitted a redundant explanation as to the image producing itself.

It happens that for the purpose of picking of a part of tissues of the affected part for a diagnosis, while an image of the affected part within the subject is formed, which is obtained with the use of the ultrasonic diagnostic system, is observed, or for the purpose of injecting medical liquid into the affected part, a puncture needle is inserted into the affected part within the subject.

There is known an ultrasonic probe for a puncture to facilitate the above-mentioned puncture operation (cf. Japanese Patent Application Laid Open Gazette Hei. 5-317309 and Japanese Utility Model Application Laid Open Gazette Hei. 5-33708). In these publication, there is proposed an ultrasonic probe for a puncture in which ultrasonic transducers, which are arranged in two directions perpendicularly intersecting each other, are provided in a unitary body, and a puncture needle guide aperture is formed so that a puncture needle may be introduced to a position at which the puncture needle appears on both two images respectively obtained through the ultrasonic transducers arranged in said two directions.

In the observation of the entire ultrasonic diagnostic works using an ultrasonic diagnostic apparatus, the puncture operation is used few times and the usual operation, such as an observation of images of the inside of the subject through moving an ultrasonic probe, is used rather much. Under such circumstances, according to the above-proposed ultrasonic probe for a puncture, the contact area to the subject is large since the ultrasonic transducers are arranged on a two-dimensional basis. This structure is suitable for operation such that the puncture needle is inserted while the ultrasonic probe for a puncture is not moved in a state that the probe is urged to a predetermined position of the subject, but is not suitable for the usual working which needs to move the ultrasonic probe. Thus, there is a need to prepare an ultrasonic probe for a usual operation in addition to preparing the ultrasonic probe for a puncture. The preparation of a plurality of types of ultrasonic probes, which are expensive, according to the presence of a puncture, causes a problem such that the cost of the ultrasonic diagnostic apparatus is increased in its entirety.

SUMMARY OF THE INVENTION

In view of the foregoing, it is therefore an object of the present invention to provide an ultrasonic probe suitable for both operation for a usual diagnosis and a puncture working, and capable of contributing to a reduction of the cost of an ultrasonic diagnostic apparatus in its entirety, and also to provide an ultrasonic diagnostic apparatus provided with such an ultrasonic probe.

To achieve the above-mentioned object, according to the present invention, there is provided an ultrasonic probe, adapted to be put to a subject, for transmitting ultrasounds to an inside of the subject and receiving the ultrasounds reflected inside the subject, said ultrasonic probe comprising:

(1) a first ultrasonic transmitter-receiver head having a plurality of first ultrasonic transducers carrying transmission and reception of ultrasounds, said plurality of first ultrasonic transducers being arranged in a predetermined first direction; and (2) a second ultrasonic transmitter-receiver head, detachably loaded onto said first ultrasonic transmitter-receiver head, having a plurality of second ultrasonic transducers carrying transmission and reception of ultrasounds, said plurality of second ultrasonic transducers being arranged in a second direction intersecting the first direction when loaded, for monitoring a state that a puncture needle to be punctured inside the subject is inserted into the inside of the subject.

The ultrasonic probe according to the present invention has the second ultrasonic transmitter-receiver head, detachably loaded onto said first ultrasonic transmitter-receiver head, for monitoring a puncture needle. The second ultrasonic transmitter-receiver head for monitoring a puncture needle aims only to monitor the puncture needle. This feature makes it possible to manufacture ultrasonic probes for a puncture at a substantially low cost and in small numbers as compared with the prior art, since it is sufficient for the present invention to obtain a resolution in such a degree that the state of a puncture is grasped, and possible to obtain more clear images as compared with the use of the ultrasonic probes for a puncture since the above-mentioned first ultrasonic transmitter-receiver head, which is the usual ultrasonic probe, is used for a diagnosis.

Further, in the ultrasonic probe according to the present invention, in the event that the second ultrasonic transmitter-receiver head is loaded onto the side (e.g. the surface directed to a direction vertical to the sheet of FIG. 16 which will be described later) of the first ultrasonic transmitter-receiver head, while a puncture needle, which appears in an ultrasonic image by the second ultrasonic transmitter-receiver head is observed, the puncture needle is punctured from a position out of a scanning plane of transmission and reception of ultrasounds by the first ultrasonic transmitter-receiver head at an almost right angle with respect to the surface of the subject, so that the tip of the puncture needle may reach the affected part with insertion of the short distance thereby dramatically improving an operability.

In the ultrasonic probe according to the present invention mentioned above, it is preferable that there is provided a puncture needle guide for introducing said puncture needle so as to travel on a tomographic plane within the subject, the tomographic plane being formed through transmission and reception of ultrasounds by said second ultrasonic transducers. The adoption of such a puncture needle guide makes it possible to surely introduce the puncture needle along the passage to the affected part thereby more dramatically improving operability.

Further, in the ultrasonic probe according to the present invention mentioned above, it is preferable that there are provided: a first cable connected to said first ultrasonic transmitter-receiver head for carrying a transmission of first drive signals for driving said first ultrasonic transducers and first received signals derived through reception of ultrasounds by said first ultrasonic transducers; a second cable connected to said second ultrasonic transmitter-receiver head for carrying a transmission of second drive signals for driving said second ultrasonic transducers and second received signals derived through reception of ultrasounds by said second ultrasonic transducers; and a fixing member for mutually fixing said first cable and said second cable on at least one point.

Usually, an ultrasonic probe is connected via a cable for transmitting signals to a main frame of an ultrasonic diagnostic apparatus. The ultrasonic probe according to the present invention has the first ultrasonic transmitter-receiver head and the second ultrasonic transmitter-receiver head. The second ultrasonic transmitter-receiver head is detachably loaded into the first ultrasonic transmitter-receiver head. Hence, it is preferable that a cable for coupling the first ultrasonic transmitter-receiver head with the main frame of the ultrasonic diagnostic apparatus is different from a cable for coupling the second ultrasonic transmitter-receiver head with the main frame of the ultrasonic diagnostic apparatus. However, if these cables are separately provided, it will be inconvenient in operation. Thus, in view of the above, it is preferable that there is provided a fixing member for mutually fixing the first cable and the second cable.

Further, in the ultrasonic probe according to the present invention mentioned above, it is preferable that there is provided detecting means for detecting a loading of said second ultrasonic transmitter-receiver head into said first ultrasonic transmitter-receiver head.

Usually, when there is no need to puncture the puncture needle in the subject, there is used only the first ultrasonic transmitter-receiver head. On the other hand, when the puncture needle is punctured in the subject, the second ultrasonic transmitter-receiver head is loaded into the first ultrasonic transmitter-receiver head so that the second ultrasonic transmitter-receiver head also performs transmission and reception of ultrasounds. As a result, an image is produced and displayed in accordance with received signals obtained by the second ultrasonic transmitter-receiver head. For this reason, there is a need to select a mode in accordance with a situation as to whether or not the puncture needle is punctured in the subject. At that time, adoption of said loading detection means makes it possible to automatically select a mode in accordance with a detection result of the loading detection means thereby improving an operability.

Further, to achieve the above-mentioned object, according to the present invention, there is provided an ultrasonic diagnostic apparatus comprising an ultrasonic probe, adapted to be put to a subject, for transmitting ultrasounds to an inside of the subject and receiving the ultrasounds reflected inside the subject, and a main frame for driving said ultrasonic probe to transmit ultrasounds therefrom, in which an image of the inside of the subject is produced and displayed in accordance with received signals derived through reception of ultrasounds by said ultrasonic probe, wherein said ultrasonic probe comprises: a first ultrasonic transmitter-receiver head having a plurality of first ultrasonic transducers carrying transmission and reception of ultrasounds, said plurality of first ultrasonic transducers being arranged in a predetermined first direction; and a second ultrasonic transmitter-receiver head, detachably loaded onto said first ultrasonic transmitter-receiver head, having a plurality of second ultrasonic transducers carrying transmission and reception of ultrasounds, said plurality of second ultrasonic transducers being arranged in a second direction intersecting the first direction when loaded, for monitoring a state that a puncture needle to be punctured inside the subject is inserted into the inside of the subject, and wherein said main frame has: a first mode in which first drive signals for driving said first ultrasonic transducers are produced, and an image of the inside of the subject is produced and displayed in accordance with first received signals derived through reception of ultrasounds by said first ultrasonic transducers; and a second mode in which both said first drive signals and second drive signals for driving said second ultrasonic transducers are produced, and both an image of the inside of the subject based on said first received signals and an image of the inside of the subject based on second received signals derived through reception of ultrasounds by said second ultrasonic transducers are produced and displayed.

The ultrasonic diagnostic apparatus according to the present invention has the ultrasonic probe according to the present invention. This feature makes it possible to contribute to a reduction of the manufacturing cost of the ultrasonic diagnostic apparatus as compared with one having both the ultrasonic probe for a diagnosis and the ultrasonic probe for a puncture proposed in prior art. Further, the ultrasonic diagnostic apparatus according to the present invention includes the ultrasonic probe according to the present invention, and in addition the main frame of the ultrasonic diagnostic apparatus has two modes mentioned above. This feature makes it possible to implement an ultrasonic diagnostic apparatus that is dramatically improved in operability as to insertion of the puncture needle in the affected part inside the subject.

In the ultrasonic diagnostic apparatus according to the present invention, when said two modes are optionally selected, it is acceptable that said main frame has a mode selection handler for selecting optionally either of the first mode and the second mode. Alternatively, it is acceptable that said ultrasonic probe has detecting means for detecting a loading of said second ultrasonic transmitter-receiver head into said first ultrasonic transmitter-receiver head, and said main frame selects the first mode or the second mode in accordance with a detection result of said detecting means.

DESCRIPTION OF THE PREFERRED EMBODIMENTS

Hereinafter, there will be described embodiments of the present invention.

Figure 1:
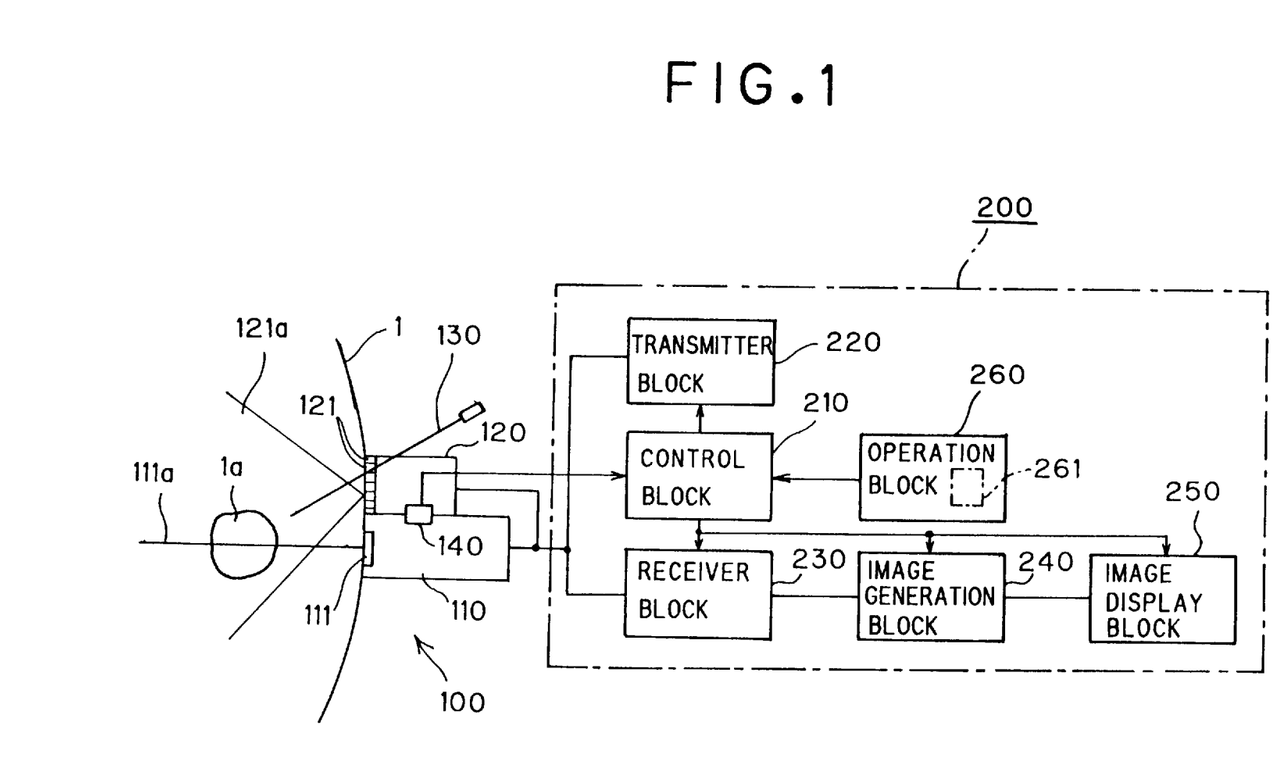
FIG. 1 is a typical illustration showing a structure of an embodiment of an ultrasonic diagnostic apparatus according to the present invention.

FIG. 1 is a typical illustration showing a structure of an embodiment of an ultrasonic diagnostic apparatus according to the present invention.

The ultrasonic diagnostic apparatus comprises an ultrasonic probe 100 and a main frame 200. The ultrasonic probe 100 comprises a first ultrasonic transmitter-receiver head 110 and a second ultrasonic transmitter-receiver head 120 detachably mounted on the first ultrasonic transmitter-receiver head 110. On the tip of the first ultrasonic transmitter-receiver head 110, there are provided a plurality of first ultrasonic transducers 111 arranged in a vertical direction with respect to the sheet of FIG. 1. The plurality of first ultrasonic transducers 111 are put to a surface of a subject 1 so that ultrasounds are transmitted and received to form a scanning plane 111a expanding in a vertical direction with respect to the sheet of FIG. 1. On the tip of the second ultrasonic transmitter-receiver head 120, there are provided a plurality of second ultrasonic transducers 121 arranged in such a manner that when the second ultrasonic transmitter-receiver head 120 is mounted on the first ultrasonic transmitter-receiver head 110, the plurality of second ultrasonic transducers 121 are in line on the sheet of FIG. 1. In the state that the second ultrasonic transmitter-receiver head 120 is mounted on the first ultrasonic transmitter-receiver head 110, the tip of the second ultrasonic transmitter-receiver head 120, together with the tip of the first ultrasonic transmitter-receiver head 110, is put to a surface of the subject 1 so that the second ultrasonic transducers 121 transmit and receive ultrasounds to form a scanning plane 121a expanding on the sheet of FIG. 1 inside the subject 1.

The ultrasonic probe 100 further comprises a sensor 140 for detecting an insertion of the second ultrasonic transmitter-receiver head 120 into the first ultrasonic transmitter-receiver head 110. A detection result of the sensor 140 is transmitted to a control block 210 of the main frame 200.

The second ultrasonic transmitter-receiver head 120 is provided with a puncture needle guide (not shown in FIG. 1) for introducing a puncture needle 130 to the affected part 1a. When the puncture needle 130 is introduced by the puncture needle guide and punctured into the subject 1, the puncture needle 130 travels toward the affected part 1a on the scanning plane 121a defined by the second ultrasonic transducers 121. The state of insertion of the puncture needle 130 appears in the image based on received signals generated from the second ultrasonic transducers 121.

The first ultrasonic transducers 111 arranged on the first ultrasonic transmitter-receiver head 110 and the second ultrasonic transducers 121 arranged on the second ultrasonic transmitter-receiver head 120 receive first drive signals and second drive signals generated from a transmitter block 220 of the main frame 200, respectively. The first ultrasonic transducers 111 and the second ultrasonic transducers 121 transmit ultrasounds toward the inside of the subject 1 and receive the ultrasounds reflected inside the subject 1 to generate first and second received signals, respectively. The first and second received signals are received by a receiver block 230 of the main frame 200 so as to be subjected to the known beam forming process. An image generating block 240 of the main frame 200 converts these received signals subjected to the beam forming process into an image signal for display. An image display block 250 of the main frame 200 displays an image based on the image signal thus converted.

The main frame 200 further comprises an operation block 260 having a handler for inputting various instructions to the ultrasonic diagnostic apparatus. The control block 210 controls the ultrasonic diagnostic apparatus in its entirety, that is, the transmitter block 220, the receiver block 230, the image generating block 240 and the image display block 250, in accordance with instructions inputted through the operation block 260.

As mentioned above, the detection result of the sensor 140 is fed to the control block 210. Upon receipt of the detection result, the control block 210 controls the ultrasonic diagnostic apparatus in its entirety in such a manner that when the second ultrasonic transmitter-receiver head 120 is not mounted on the first ultrasonic transmitter-receiver head 110, the transmitter block 220 generates the first drive signals for driving the first ultrasonic transducers 111, and the image display block 250 displays an image inside the subject 1 based on the first received signals obtained by means of receiving ultrasounds through the first ultrasonic transducers 111 (this is referred to as a "first model"). On the other hand, when the second ultrasonic transmitter-receiver head 120 is mounted on the first ultrasonic transmitter-receiver head 110, the control block 210 controls the ultrasonic diagnostic apparatus in its entirety in such a manner that the transmitter block 220 generates both the first drive signals for driving the first ultrasonic transducers 111 and the second drive signals for driving the second ultrasonic transducers 121, and the image display block 250 displays an image inside the subject 1 based on the first received signals obtained by means of receiving ultrasounds through the first ultrasonic transducers 111 and an image inside the subject 1 based on the second received signals obtained by means of receiving ultrasounds through the second ultrasonic transducers 121 (this is referred to as a "second mode").

According to the present embodiment, as mentioned above, a mode selection is performed in accordance with a detection result of the sensor 140. However, it is acceptable that in addition to the use of the sensor 140 the operation block 260 is provided with a mode selection button 261. In this case, whenever the mode selection button 261 is depressed, a mode switching is performed from the first mode to the second mode or from the second mode to the first mode. Further, in case of the use of both the sensor 140 and the mode selection button 261, it is acceptable to provide such an arrangement that for example, when a detection result of the sensor 140 is changed, a mode is switched to the mode associated with a detection result after the change, and the mode is set up as the initial value and thereafter the mode selection is performed by depression of the mode selection button 261.

Figure 2:
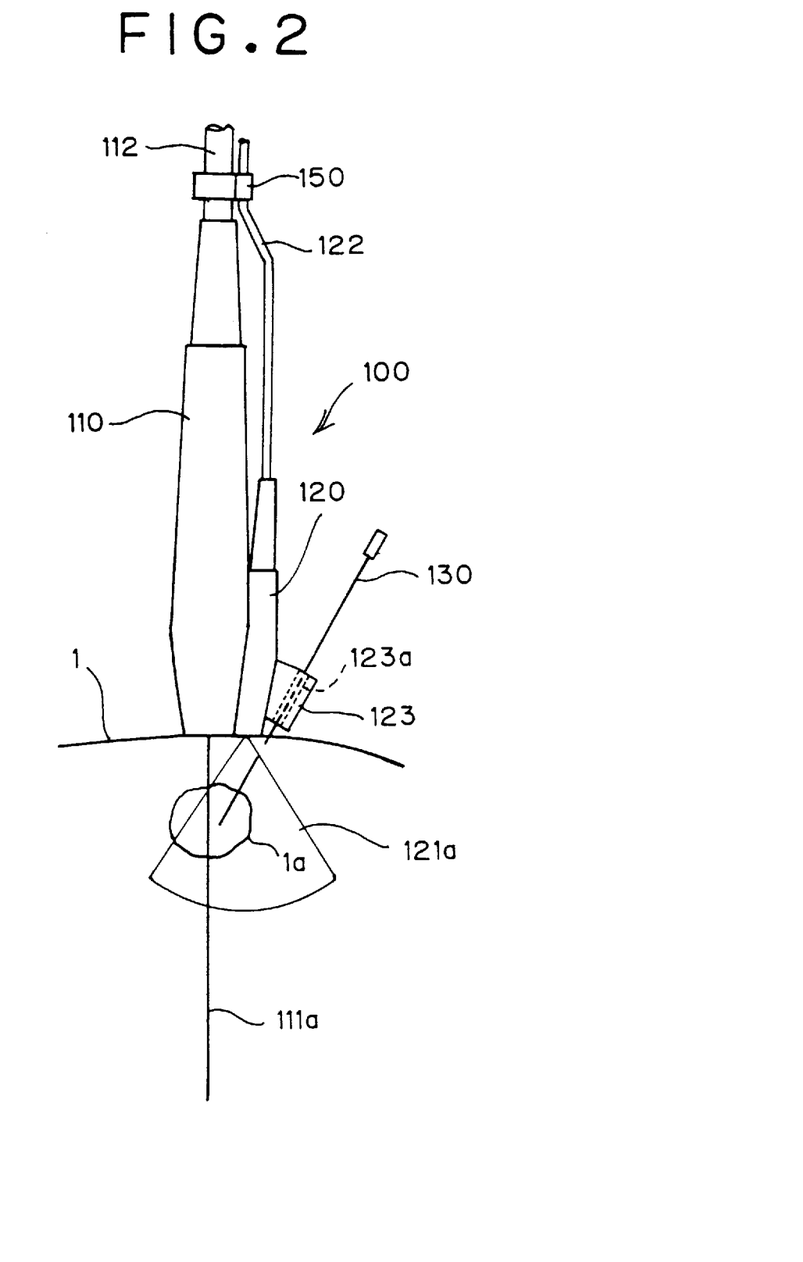
FIG. 2 is a side view of the first embodiment of an ultrasonic probe according to the present invention, the ultrasonic probe being adopted in the ultrasonic diagnostic apparatus shown in FIG. 1.
Figure 3:
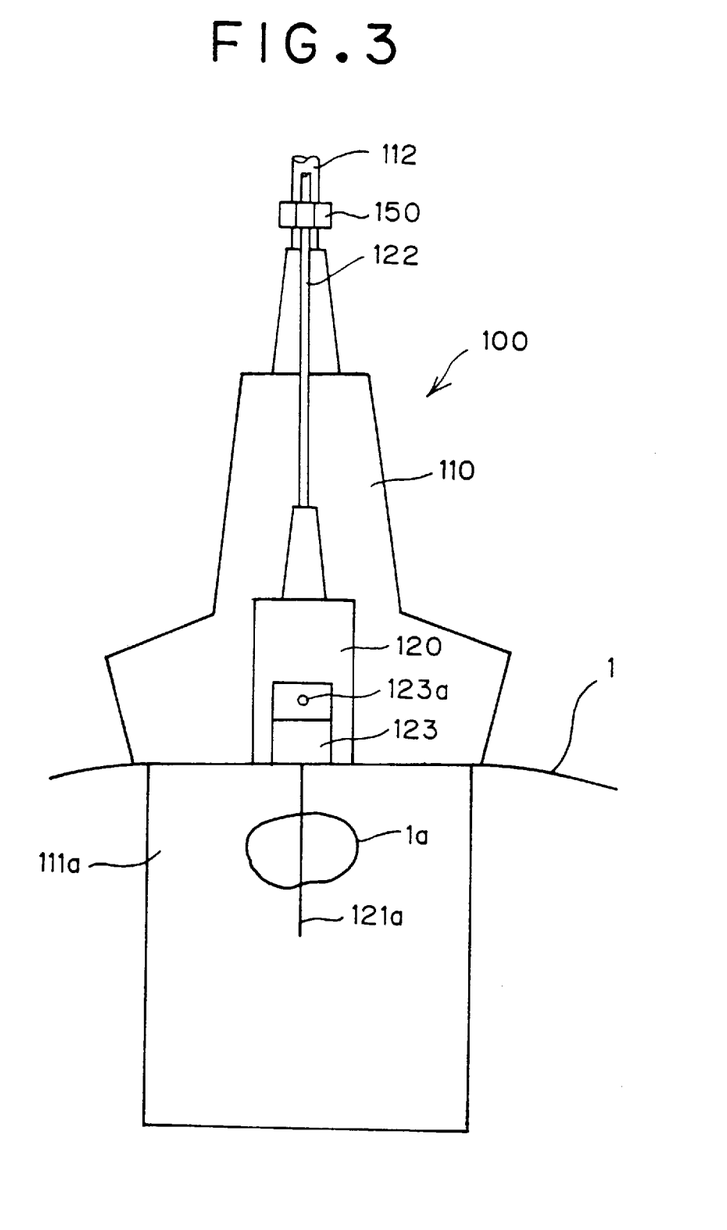
FIG. 3 is a front view of the first embodiment of an ultrasonic probe according to the present invention, the ultrasonic probe being adopted in the ultrasonic diagnostic apparatus shown in FIG. 1.
Figure 4:
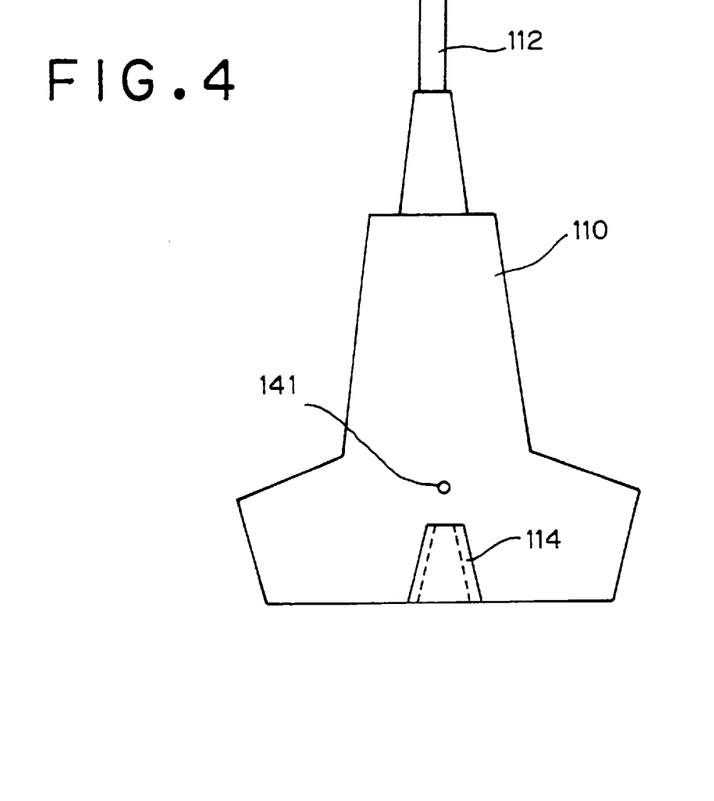
FIG. 4 is a front elevation of the first ultrasonic transmitter-receiver head constituting the ultrasonic probe shown in FIGS. 2 and 3.
Figure 5:
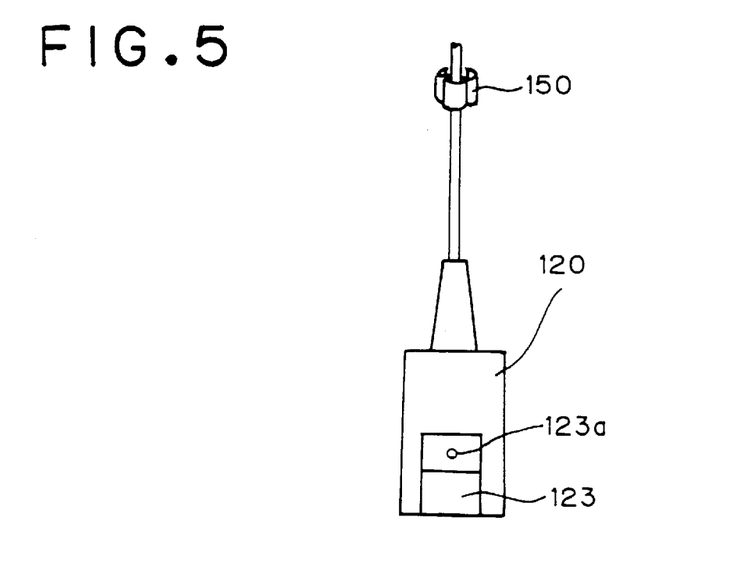
FIG. 5 is a front elevation of the second ultrasonic transmitter-receiver head constituting the ultrasonic probe shown in FIGS. 2 and 3.
Figure 6:
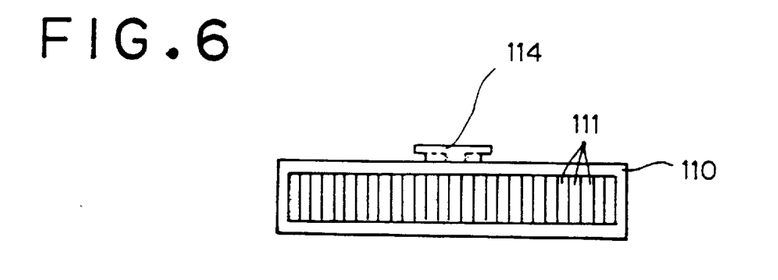
FIG. 6 is a bottom plan view of the first ultrasonic transmitter-receiver head.
Figure 7:
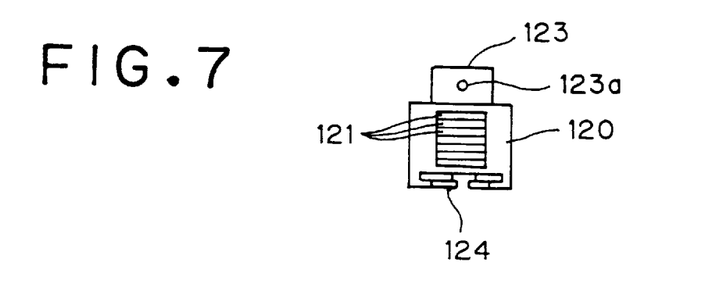
FIG. 7 is a bottom plan view of the second ultrasonic transmitter-receiver head.

FIGS. 2 and 3 are side and front views of the first embodiment of an ultrasonic probe according to the present invention, the ultrasonic probe being adopted in the ultrasonic diagnostic apparatus shown in FIG. 1, respectively. FIGS. 4 and 5 are front elevations of the first and second ultrasonic transmitter-receiver head constituting the ultrasonic probe shown in FIGS. 2 and 3, respectively. FIGS. 6 and 7 are bottom plan views of the first ultrasonic transmitter-receiver head and the second ultrasonic transmitter-receiver head, respectively.

In these FIGS. 2–7, the same parts are denoted by the same reference numbers as those of FIG. 1.

The first ultrasonic transmitter-receiver head 110 has a loading section 114 (FIGS. 4 and 6) for loading the second ultrasonic transmitter-receiver head 120. On the other hand, the second ultrasonic transmitter-receiver head 120 has a loading section 124 (FIG. 7) having a configuration adapted to engage with the loading section 114 of the first ultrasonic transmitter-receiver head 110. The engagement of these loading sections 114 and 124 permits the second ultrasonic transmitter-receiver head 120 to be loaded into the first ultrasonic transmitter-receiver head 110, as shown in FIGS. 2 and 3.

The first ultrasonic transmitter-receiver head 110 is an ultrasonic probe for a usual diagnosis and is made as small and as thin as possible taking into account the operability. Thus, the loading section 114 of the first ultrasonic transmitter-receiver head 110 is formed with a configuration projecting from the main frame of the first ultrasonic transmitter-receiver head 110. In order to avoid a damage of the operability of the first ultrasonic transmitter-receiver head 110 as the ultrasonic probe for a usual diagnosis, it is preferable that the loading section 114 is also formed with a configuration as small and as thin as possible.

Near the loading section 114 of the first ultrasonic transmitter-receiver head 110, there is provided a projection pin 141 constituting the sensor 140 shown in FIG. 1. The projection pin 141 is so arranged that when the second ultrasonic transmitter-receiver head 120 is loaded into the first ultrasonic transmitter-receiver head 110, the projection pin 141 is pushed by the second ultrasonic transmitter-receiver head 120 to move inside the first ultrasonic transmitter-receiver head 110.

Figure 8:
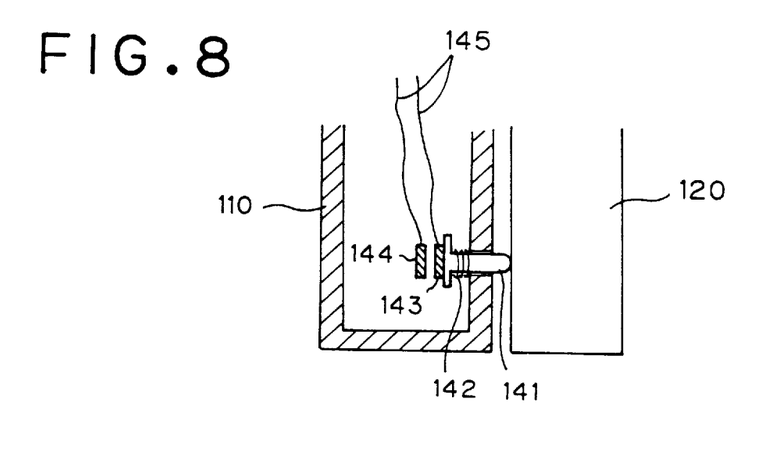
FIG. 8 is a typical illustration of a sensor including a projection pin.

FIG. 8 is a typical illustration of a sensor including a projection pin.

In the state that the second ultrasonic transmitter-receiver head 120 is not loaded into the first ultrasonic transmitter-receiver head 110, the projection pin 141 projects from the first ultrasonic transmitter-receiver head 110 by a spring force of a spring 142. When the second ultrasonic transmitter-receiver head 120 is loaded into the first ultrasonic transmitter-receiver head 110, the projection pin 141 is pushed by the second ultrasonic transmitter-receiver head 120 to move inside the first ultrasonic transmitter-receiver head 110 against the spring force of the spring 142. At that time, a contact 143 located at the projection pin end comes into contact with a fixed contact 144. Information as to whether the contact 143 comes into contact with the contact 144, that is, information indicative of whether the second ultrasonic transmitter-receiver head 120 is loaded into the first ultrasonic transmitter-receiver head 110, is transmitted via a lead wire 145 to the control block 210 of the main frame 200.

Figure 9:
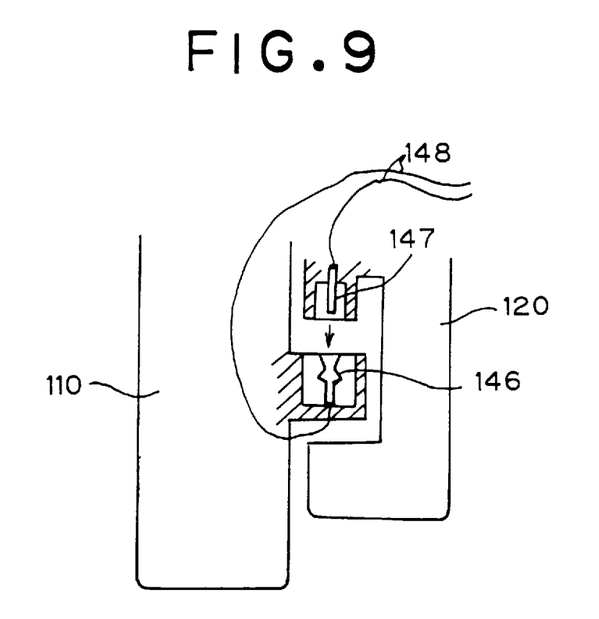
FIG. 9 is a view showing another structural example of the sensor shown in FIG. 1.

FIG. 9 is a view showing another structural example of the sensor shown in FIG. 1.

According to the present example of the sensor, the first ultrasonic transmitter-receiver head 110 is provided with a female contact 146, while the second ultrasonic transmitter-receiver head 120 is provided with a male contact 147. Loading of the first ultrasonic transmitter-receiver head 110 into the second ultrasonic transmitter-receiver head 120 allows the female contact 146 to be engaged with the male contact 147. Information as to whether the contact 146 is engaged with the male contact 147, that is, information indicative of whether the second ultrasonic transmitter-receiver head 120 is loaded into the first ultrasonic transmitter-receiver head 110, is transmitted via a lead wire 148 to the control block 210 of the main frame 200.

Again referring to FIGS. 2–7, the explanation of the ultrasonic probe will be continued.

As most clearly shown in FIG. 2, the second ultrasonic transmitter-receiver head 120 of the ultrasonic probe 100 is provided with a puncture needle guide block 123 having a puncture needle guide passage 123a for introducing the puncture needle 130 into the subject 1.

The puncture needle 130 is inserted into the puncture needle guide passage 123a so as to to puncture the subject 1 and travel on a scanning plane 121a of the second ultrasonic transducers 121 to the affected part 1a. The state of the insertion of the puncture needle 130 into the subject 1 appears on an image based on the second received signals obtained by the second ultrasonic transducers 121.

Connected to the first ultrasonic transmitter-receiver head 110 is a one end of the first cable 112. Connected to the second ultrasonic transmitter-receiver head 120 is a one end of the second cable 122. Both the first cable 112 and the second cable 122 are mutually fixed by a fixing member 150. The first cable 112 serves to transmit the first drive signals generated by the transmitter block 220 of the main frame 200 to the first ultrasonic transducers 111 and also to transmit the first received signals obtained through receiving of ultrasounds by the first ultrasonic transducers 111 to the receiver block 230 of the main frame 200. In a similar fashion to that of the first cable 112, the second cable 122 serves to transmit the second drive signals generated by the transmitter block 220 of the main frame 200 to the second ultrasonic transducers 121 and also to transmit the second received signals obtained through receiving of ultrasounds by the second ultrasonic transducers 121 to the receiver block 230 of the main frame 200. A detection signal, which is derived from the sensor 140 (FIG. 1) for detecting an insertion of the second ultrasonic transmitter-receiver head 120 into the first ultrasonic transmitter-receiver head 110, is transmitted to the control block 210 of the main frame 200 via the first cable 112 or the second cable 122, or both the first cable 112 and the second cable 122 in accordance with the structure of the sensors (e.g. FIGS. 8 and 9).

Figure 10:
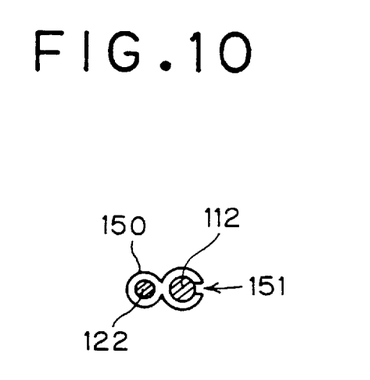
FIG. 10 is a sectional view of a fixing member.

FIG. 10 is a sectional view of the fixing member 150 shown in FIGS. 2 and 3.

The fixing member 150 is fixed on the second cable 122. The first cable 112 is pushed through an opening 151, so that the first cable 112 is fixed on the second cable 122. It is also acceptable that the fixing member 150 is fixed on the end of the first cable 112, and the second cable 122 is detachably mounted on the first cable 112.

Figure 11:
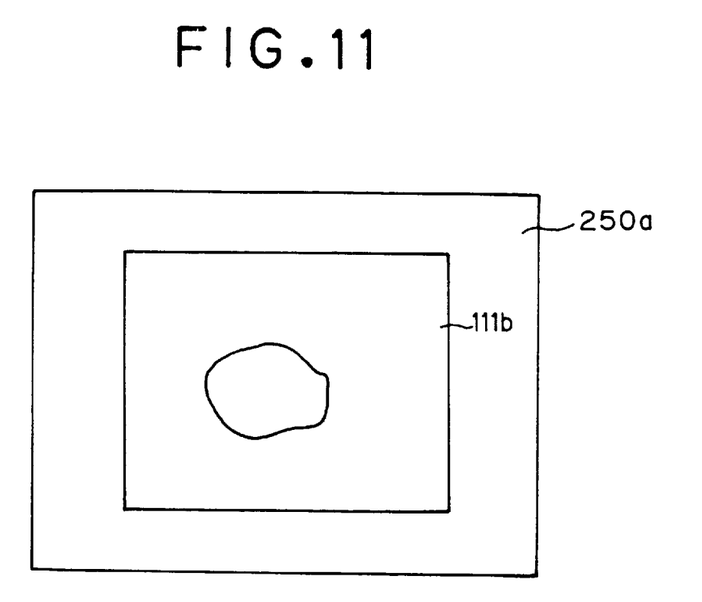
FIG. 11 is a typical illustration of a tomographic image of the inside of the subject to be displayed on a display screen of the image display unit shown in FIG. 1.
Figure 12:
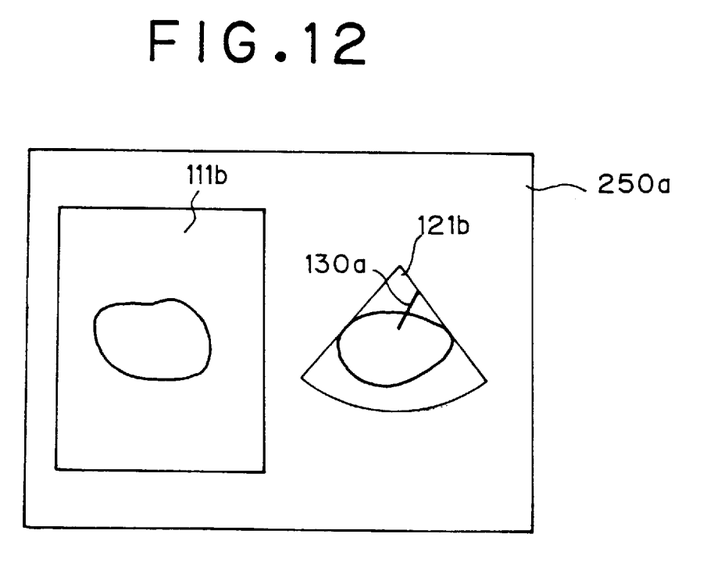
FIG. 12 is a typical illustration of a tomographic image of the inside of the subject to be displayed on a display screen of the image display unit shown in FIG. 1.

Each of FIGS. 11 and 12 is a typical illustration of a tomographic image of the inside of the subject to be displayed on a display screen of the image display unit 250 shown in FIG. 1.

FIG. 11 relates to a tomographic image in the first mode using only the the first ultrasonic transmitter-receiver head 110, of the first ultrasonic transmitter-receiver head 110 and the second ultrasonic transmitter-receiver head 120. In FIG. 11, there is displayed on a display screen 250a a tomographic image 111b on the same plane as a scanning plane 111a on the basis of the first received signals obtained by the first ultrasonic transducers 111. Thus, in a case where a diagnosis is carried out in connection with the inside of the subject 1, other than a case where the puncture needle 130 is punctured into the subject 1, only the first ultrasonic transmitter-receiver head 110 is used to produce and display images of the inside of the subject 1.

FIG. 12 relates to tomographic images in the second mode using both the first ultrasonic transmitter-receiver head 110 and the second ultrasonic transmitter-receiver head 120. In FIG. 12, there are displayed on the display screen 250a a tomographic image 111b based on the first received signals obtained by the first ultrasonic transducers 111 and a tomographic image 121b based on the second received signals obtained by the second ultrasonic transducers 121. On the tomographic image 121b based on the second received signals, there appears also a shadow 130a of the puncture needle which is punctured into the subject 1.

According to the first embodiment mentioned above, it is allowed to insert the puncture needle 130 into the subject 1 in the state that the puncture needle 130 stands (near vertically with respect to the surface of the subject 1). Thus, this feature makes it reduce the stroke of insertion, thereby extremely improving operability.

Figure 13:
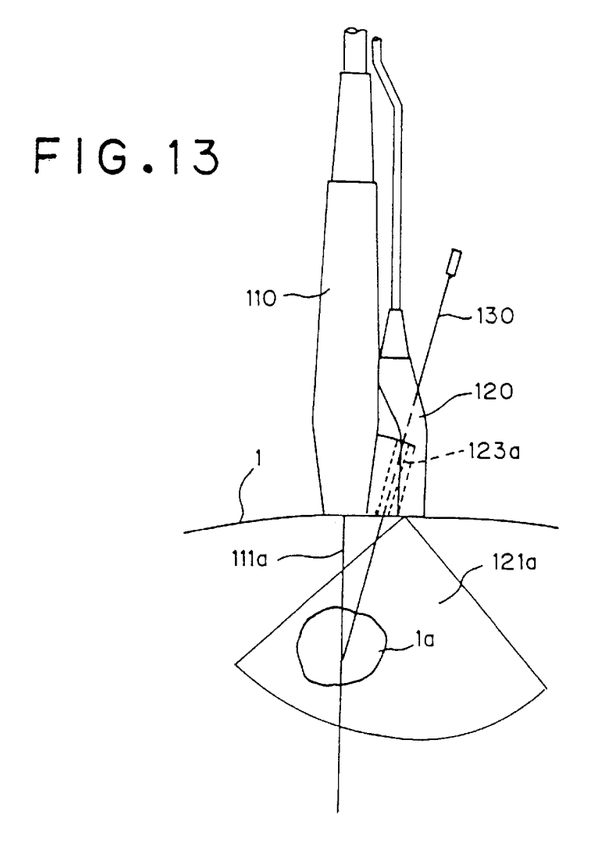
FIG. 13 is a side view of the second embodiment of an ultrasonic probe according to the present invention, the ultrasonic probe being adopted in the ultrasonic diagnostic apparatus shown in FIG. 1.
Figure 14:
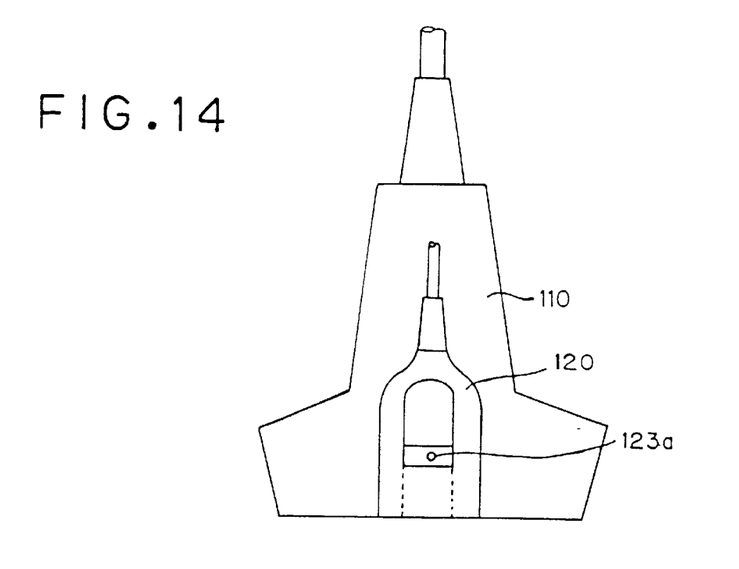
FIG. 14 is a front view of the second embodiment of an ultrasonic probe according to the present invention, the ultrasonic probe being adopted in the ultrasonic diagnostic apparatus shown in FIG. 1.
Figure 15:
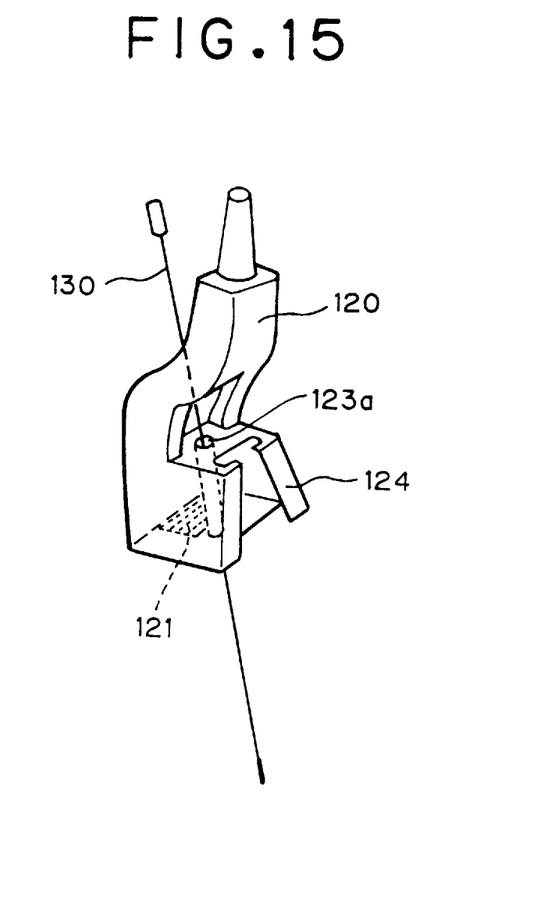
FIG. 15 is a perspective view of the second ultrasonic transmitter-receiver head constituting the ultrasonic probe shown in FIGS. 13 and 14.

FIGS. 13 and 14 are side and front views of the second embodiment of an ultrasonic probe according to the present invention, the ultrasonic probe being adopted in the ultrasonic diagnostic apparatus shown in FIG. 1, respectively. FIG. 15 is a perspective view of the second ultrasonic transmitter-receiver head constituting the ultrasonic probe shown in FIGS. 13 and 14. In those figures, the substantially same parts are denoted by the same reference numbers as those of FIGS. 2–7.

According to the second embodiment of an ultrasonic probe according to the present invention, as shown in FIGS. 13–15, there is provided near a loading section 124 of the second ultrasonic transmitter-receiver head 120 a puncture needle guide passage 123a for introducing the puncture needle 130. That is, it is so arranged that when the second ultrasonic transmitter-receiver head 120 is loaded onto the first ultrasonic transmitter-receiver head 110, the puncture needle 130 is located near the first ultrasonic transmitter-receiver head 110. Such an arrangement allows the puncture needle 130 to be inserted into the subject 1 in the state where the puncture needle 130 stands nearer vertically as compared with that of the first embodiment. Thus, this feature makes it possible to further reduce the stroke of insertion, thereby further improving an operability.

According to the respective embodiments mentioned above, while the puncture needle guide passage for introducing the puncture needle is provided on the second ultrasonic transmitter-receiver head, it is acceptable that the first ultrasonic transmitter-receiver head is provided with the puncture needle guide such as the puncture needle guide passage. Alternatively, it is acceptable that no puncture needle guide is provided, and insertion of the puncture needle is left to an operator's (e.g. doctor's) discretion.

Figure 16:
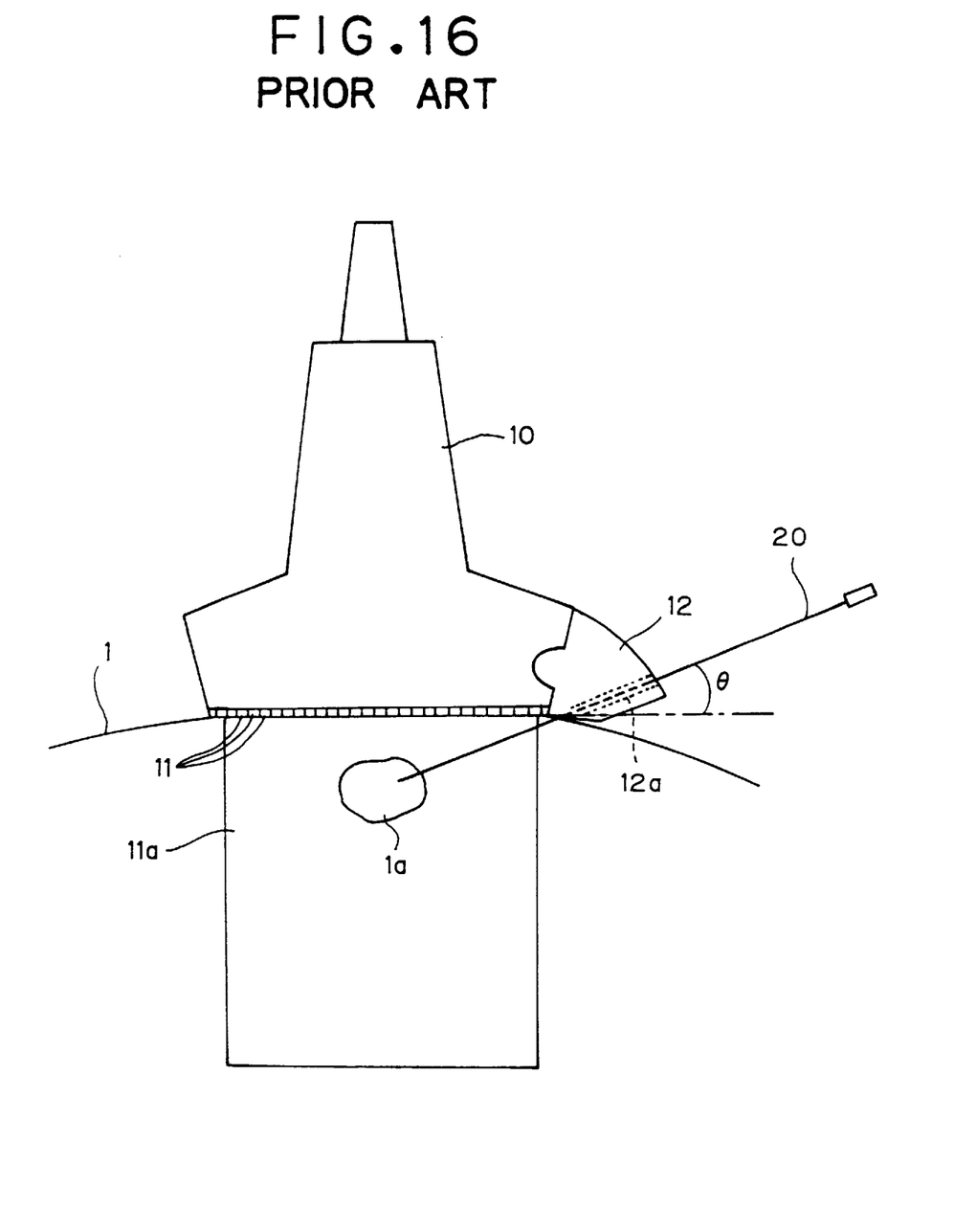
FIG. 16 is a typical illustration of an ultrasonic probe having a puncture needle guide useful for inserting a puncture needle into the subject.

FIG. 16 is a typical illustration of an ultrasonic probe having a puncture needle guide useful for inserting a puncture needle into the subject.

On the tip of an ultrasonic probe 10, there are provided a large number of ultrasonic transducers 11 arranged in a horizontal direction in FIG. 16. The tip of an ultrasonic probe 10 is put to a surface of the subject 1, and transmission and reception of ultrasounds into the subject are repeated so that a scan line shifts (or scans) on a scan surface 11a. A main frame of the ultrasonic diagnostic system (not shown) creates a tomographic image of the subject on the same plane as the scan surface 11a in accordance with received signal obtained through ultrasonic scanning on the scan surface 11a.

The ultrasonic probe 10 shown in FIG. 16 is used for a so-called linear scan in which scan lines vertically extending in the subject 1 are moved in parallel on the scan surface 11a to generate a tomographic image of a rectangular section as the scan surface 11a. In case of the linear scan, there is needed an ultrasonic probe large in its caliber as shown in FIG. 16.

It is assumed that an affected part 1a exists inside the subject 1 and a puncture needle 20 is inserted into the affected part 1a.

A puncture needle adapter 12 having a puncture needle guide aperture 12a is fixed on one end of the ultrasonic transducers 11 with respect to the arrangement direction thereof. The puncture needle 20 is inserted into puncture needle guide aperture 12a, and further inserted inside the subject 1 in such a manner that the tip of the puncture needle 20 reaches the affected part 1a while a tomographic image including a shadow of the affected part 1a is observed. The puncture needle guide aperture 12a is arranged in such a manner that the puncture needle 20 may travel on the scan surface 11a inside the subject 1. Consequently, when the puncture needle 20 is inserted inside the subject 1, the puncture needle 20 appears in a tomographic image on the scan surface 11a from the initial stage of the insertion. Thus, it is possible to surely introduce the tip of the puncture needle 20 to the affected part 1a.

For example, in a case where a diagnosis for the thyroid gland or the mammary gland is performed, in many cases, the affected part 1a is relatively near a surface of the human body, and an ultrasonic probe for observation of the thyroid gland or the mammary gland uses relatively high frequency of ultrasounds. In the case where the affected part 1a is near a surface of the human body, it is necessary for insertion of the puncture needle 20 into the inside of the subject 1 to insert the puncture needle 20 from a position located away from the affected part 1a with a shallow angle (angle θ shown in FIG. 16 is small) as shown in FIG. 16. This involves an enlargement of a shape of the puncture needle adapter 12. Further, according to the above-mentioned ultrasonic probe system, it is obliged to provide a large insertion stroke for the puncture needle into the subject. This raises such a problem that the ultrasonic probe system is inferior in operability.

Further, even in a case where a skilled doctor punctures the puncture needle 20 into the inside of the subject 1 without the use of the puncture needle adapter 12, when the doctor inserts the puncture needle 20 into the inside of the subject 1 while observing its situation, there is a need to insert the puncture needle 20 so that the puncture needle 20 travels on the scan surface 11a. For this reason, in a similar fashion to that of the use of the puncture needle adapter 12 shown in FIG. 16, there is a need to insert the puncture needle 20 from a position located away from the affected part 1a with a shallow angle for a long distance. Also in this case, there arises such a problem that an insertion work for the puncture needle 20 is difficult to do.

On the other hand, the above-mentioned ultrasonic probe for a puncture as proposed in prior art has no caliber sufficient for performing the linear scan, since it has a two-dimensional spread to the subject. Therefore, it is difficult to perform a puncture working through the observation of images obtained by the linear scan with the use of the ultrasonic probe for a puncture. In view of the foregoing, the present invention is applied to a linear scan type of ultrasonic probe for a diagnosis in which the first ultrasonic transmitter-receiver head 110 according to anyone of the above-mentioned embodiments is given with a linear scan type of one, and the second ultrasonic transmitter-receiver head for a puncture is detachably mounted on the linear scan type of first ultrasonic transmitter-receiver head. This feature makes it possible to readily perform a puncture working for, for example, the affected part near the body surface, while images easy for a diagnosis are displayed by the linear scan and the insertion state of the puncture needle is observed.

As mentioned above, according to the present invention, it is possible to implement an ultrasonic probe suitable for both the uses of a usual diagnosis and a puncture and capable of contributing to a reduction of the cost, and an ultrasonic diagnostic apparatus having such an ultrasonic probe.

While the present invention has been described with reference to the particular illustrative embodiments, it is not to be restricted by those embodiments but only by the appended claims. It is to be appreciated that those skilled in the art can change or modify the embodiments without departing from the scope and spirit of the present invention.

We claim:

1. An ultrasonic probe, adapted to be put to a subject, for transmitting ultrasounds to an inside of the subject and receiving the ultrasounds reflected from inside the subject, said ultrasonic probe comprising:

a first ultrasonic transmitter-receiver head having a plurality of first ultrasonic transducers carrying transmission and reception of ultrasounds, said plurality of first ultrasonic transducers being arranged in a predetermined first direction; and a second ultrasonic transmitter-receiver head, detachably loaded onto said first ultrasonic transmitter-receiver head, having a plurality of second ultrasonic transducers carrying transmission and reception of ultrasounds, said plurality of second ultrasonic transducers being arranged in a second direction intersecting the first direction when loaded, for monitoring a state where a puncture needle to be punctured inside the subject is inserted into the inside of the subject.

2. An ultrasonic probe according to claim 1, further comprising a puncture needle guide for introducing said puncture needle so as to travel on a tomographic plane within the subject, the tomographic plane being formed through transmission and reception of ultrasounds by said second ultrasonic transducers.

3. An ultrasonic probe according to claim 1, further comprising:

a first cable connected to said first ultrasonic transmitter-receiver head for carrying a transmission of first drive signals for driving said first ultrasonic transducers and first received signals derived through reception of ultrasounds by said first ultrasonic transducers;

a second cable connected to said second ultrasonic transmitter-receiver head for carrying a transmission of second drive signals for driving said second ultrasonic transducers and second received signals derived through reception of ultrasounds by said second ultrasonic transducers; and a fixing member for mutually fixing said first cable and said second cable at at least one point.

4. An ultrasonic probe according to claim 1, further comprising detecting means for detecting a loading of said second ultrasonic transmitter-receiver head into said first ultrasonic transmitter-receiver head.

5. An ultrasonic diagnostic apparatus comprising an ultrasonic probe, adapted to be put to a subject, for transmitting ultrasounds to an inside of the subject and receiving the ultrasounds reflected inside the subject, and a main frame for driving said ultrasonic probe to transmit ultrasounds therefrom, in which an image of the inside of the subject is produced and displayed in accordance with received signals derived through reception of ultrasounds by said ultrasonic probe, wherein said ultrasonic probe comprises:

a first ultrasonic transmitter-receiver head having a plurality of first ultrasonic transducers carrying transmission and reception of ultrasounds, and plurality of first ultrasonic transducers being arranged in a predetermined first direction; and a second ultrasonic transmitter-receiver head, detachably loaded onto said first ultrasonic transmitter-receiver carrying transmission and reception of ultrasounds, said plurality of second ultrasonic transducers being arranged in a second ultrasonic transducers carrying transmission and reception of ultrasounds, said plurality of second ultrasonic transducers being arranged in a second direction intersecting the first direction when loaded, for monitoring a state that a puncture needle to be punctured inside the subject is inserted into the inside of the subject, and wherein said main frame includes:

a first mode in which first drive signals for driving said first ultrasonic transducers are produced, and an image of the inside of the subject is produced and displayed in accordance with first received signals derived through reception of ultrasounds by said first ultrasonic transducers; and a second mode in which both said first drive signals and second drive signals for driving said second ultrasonic transducers are produced, and both an image of the inside of the subject based on said first received signals and an image of the inside of the subject based on second received signals derived through reception of ultrasounds by said second ultrasonic transducers are produced and displayed.

6. An ultrasonic diagnostic apparatus according to claim 5, wherein said main frame has a mode selection handler for selecting optionally either of the first mode and the second mode.

7. An ultrasonic diagnostic apparatus according to claim 5, wherein said ultrasonic probe has detecting means for detecting a loading of said second ultrasonic transmitter-receiver head into said first ultrasonic transmitter-receiver head, and said main frame selects the first mode or the second mode in accordance with a detection result of said detecting means.

8. An ultrasonic probe, comprising:

a first ultrasonic transmitter-receiver head having a plurality of first transducers in a first plane formed on a surface thereof meant to contact a subject;

a second ultrasonic transmitter-receiver head having a plurality of second transducers formed on a surface thereof meant to contact the subject, said second transducers being disposed in a direction that intersects a direction of the first transducers and in a second plane different from said first plane;

wherein said second ultrasonic transmitter-receiver head is detachably joined with said first ultrasonic transmitter-receiver head, and said second ultrasonic transmitter-receiver head monitors a state where a puncture needle is inserted into the inside of the subject.

* * * * *